US009206932B2

(12) United States Patent
Colman et al.

(10) Patent No.: US 9,206,932 B2
(45) Date of Patent: Dec. 8, 2015

(54) TUBE VERIFIER

(71) Applicant: ORIDION MEDICAL (1987) LTD., Jerusalem (IL)

(72) Inventors: Joshua Lewis Colman, Jerusalem (IL); Zion Botesazan, Cochav Hashacar (IL); Gal Itzhak, Jerusalem (IL)

(73) Assignee: Oridion Medical (1987) Ltd., Jerusalem (IL)

( * ) Notice: Subject to any disclaimer, the term of this patent is extended or adjusted under 35 U.S.C. 154(b) by 0 days.

(21) Appl. No.: 14/605,978

(22) Filed: Jan. 26, 2015

(65) Prior Publication Data

US 2015/0137507 A1    May 21, 2015

Related U.S. Application Data

(63) Continuation of application No. 14/255,724, filed on Apr. 17, 2014, now Pat. No. 8,967,461, which is a continuation of application No. 13/946,994, filed on Jul. 19, 2013, now Pat. No. 8,720,772, which is a continuation of application No. 12/811,361, filed as application No. PCT/IL2007/001632 on Dec. 31, 2007, now Pat. No. 8,763,892.

(51) Int. Cl.
*G06K 19/077* (2006.01)
*G06K 19/06* (2006.01)
(Continued)

(52) U.S. Cl.
CPC ............... *F16L 37/24* (2013.01); *A61M 39/10* (2013.01); *B01L 3/565* (2013.01); *G01B 11/26* (2013.01); *G01N 35/00732* (2013.01); *G06F 17/30* (2013.01); *G06K 19/0614* (2013.01); *G06K 19/06028* (2013.01); *G06K 19/07758* (2013.01); *A61M 25/0014* (2013.01); *A61M 2039/1044* (2013.01); *A61M 2039/1094* (2013.01); *A61M 2205/276* (2013.01); *A61M 2205/6018* (2013.01); *A61M 2205/6054* (2013.01); *A61M 2205/6063* (2013.01); *A61M 2205/6072* (2013.01); *B01L 2200/143* (2013.01);
(Continued)

(58) Field of Classification Search
CPC .......... B01L 2300/168; F16L 2201/00; F16L 2201/60; F16L 2201/10; F16L 37/24; G06K 19/0614; A61M 2205/6018; A61M 2205/6063
See application file for complete search history.

(56) References Cited

U.S. PATENT DOCUMENTS 3,880,148 A    4/1975  Kanehira
4,050,450 A    9/1977  Polanyi
(Continued)

FOREIGN PATENT DOCUMENTS

JP    S53-095187    12/1976
JP    2-108934    4/1990
(Continued)

OTHER PUBLICATIONS

JP 9-301901 Office Action dated Apr. 17, 2007—includes partial translation of JP 4-55544.

*Primary Examiner* — Daniel Walsh
(74) *Attorney, Agent, or Firm* — Rodney J. Fuller; Booth Udall Fuller, PLC

(57) ABSTRACT

There is provided a tube connector for connecting between a fluid sampling tube and a fluid analyzer, the tube connector includes an end face adapted to identify the tube connector, said end face comprising a reflecting surface having one or more reflective regions adapted to reflect light at a predetermined range of wavelengths.

8 Claims, 3 Drawing Sheets

(51) Int. Cl.
*F16L 37/24* (2006.01)
*A61M 39/10* (2006.01)
*B01L 3/00* (2006.01)
*G01N 35/00* (2006.01)
*G06F 17/30* (2006.01)
*G01B 11/26* (2006.01)
*A61M 25/00* (2006.01)

(52) U.S. Cl.
CPC .... *B01L2300/022* (2013.01); *B01L 2300/0627* (2013.01); *B01L 2300/168* (2013.01); *F16L 2201/10* (2013.01); *Y10T 29/49826* (2015.01)

(56) References Cited

U.S. PATENT DOCUMENTS

| | | | |
|---|---|---|---|
| 4,374,397 A | 2/1983 | Mir | |
| 4,511,251 A | 4/1985 | Falcoff | |
| 4,650,475 A | 3/1987 | Smith | |
| 4,761,543 A | 8/1988 | Hayden | |
| 4,800,823 A | 1/1989 | Hyatt | |
| 4,816,418 A | 3/1989 | Mack | |
| 4,863,819 A | 9/1989 | Drexler | |
| 4,917,491 A | 4/1990 | Ring | |
| 4,940,050 A | 7/1990 | Forssmann | |
| 5,200,604 A | 4/1993 | Rudko | |
| 5,279,576 A | 1/1994 | Loo | |
| 5,369,529 A | 11/1994 | Kuo | |
| 5,390,964 A | 2/1995 | Gray, Jr. | |
| 5,417,733 A | 5/1995 | Wesson | |
| 5,437,284 A | 8/1995 | Trimble | |
| 5,474,060 A | 12/1995 | Evans | |
| 5,517,313 A | 5/1996 | Colvin, Jr. | |
| 5,531,698 A | 7/1996 | Olsen | |
| 5,746,976 A | 5/1998 | Yamada | |
| 5,997,502 A | 12/1999 | Reilly | |
| 6,041,688 A | 3/2000 | Woznica | |
| 6,203,214 B1 | 3/2001 | Wesson | |
| 6,325,422 B1 | 12/2001 | Verkaart | |
| 6,437,316 B1 * | 8/2002 | Colman et al. | 250/222.1 |
| 6,468,424 B1 * | 10/2002 | Donig et al. | 210/232 |
| 6,489,169 B1 | 12/2002 | Cohen | |
| 6,510,857 B1 | 1/2003 | Middleton | |
| 6,550,952 B1 | 4/2003 | Hulse | |
| 7,128,348 B2 | 10/2006 | Kawamura | |
| 7,298,274 B2 * | 11/2007 | Chen et al. | 340/572.8 |
| 7,591,181 B2 | 9/2009 | Ales | |
| 8,197,087 B2 | 6/2012 | Sobue | |
| 8,425,464 B2 | 4/2013 | Patrick | |
| 8,585,649 B2 | 11/2013 | Butterfield | |
| 8,720,772 B2 * | 5/2014 | Colman et al. | 235/375 |
| 8,749,396 B2 | 6/2014 | Maggiore | |
| 8,763,892 B2 * | 7/2014 | Colman et al. | 235/375 |
| 8,763,895 B2 * | 7/2014 | Colman et al. | 235/375 |
| 8,967,461 B2 * | 3/2015 | Colman et al. | 235/375 |
| 2001/0031928 A1 | 10/2001 | Orr | |
| 2001/0051804 A1 | 12/2001 | Mulier | |
| 2001/0056258 A1 | 12/2001 | Evans | |
| 2002/0017602 A1 | 2/2002 | Gseller | |
| 2002/0025828 A1 | 2/2002 | Turetzky | |
| 2002/0028434 A1 | 3/2002 | Goix | |
| 2002/0092186 A1 | 7/2002 | Napier | |
| 2002/0103711 A1 | 8/2002 | Karas | |
| 2003/0127094 A1 | 7/2003 | Roberts | |
| 2004/0004128 A1 | 1/2004 | Pettinelli | |
| 2004/0098276 A1 | 5/2004 | Blazey | |
| 2004/0196143 A1 | 10/2004 | Crump | |
| 2005/0006481 A1 | 1/2005 | Han | |
| 2005/0273016 A1 * | 12/2005 | Colman et al. | 600/529 |
| 2005/0277873 A1 | 12/2005 | Stewart | |
| 2006/0000293 A1 | 1/2006 | Rieder | |
| 2006/0029519 A1 | 2/2006 | Nakaya | |
| 2006/0094466 A1 | 5/2006 | Tran | |
| 2006/0189858 A1 | 8/2006 | Sterling | |
| 2006/0200568 A1 | 9/2006 | Kim | |
| 2006/0258986 A1 | 11/2006 | Hunter | |
| 2006/0284061 A1 | 12/2006 | Yeoh | |
| 2007/0096844 A1 | 5/2007 | Baird | |
| 2007/0159337 A1 | 7/2007 | Tethrake | |
| 2007/0164919 A1 | 7/2007 | Lee | |
| 2007/0167919 A1 | 7/2007 | Nemoto | |
| 2007/0168266 A1 | 7/2007 | Questembert | |
| 2007/0181790 A1 | 8/2007 | Chin | |
| 2008/0021274 A1 | 1/2008 | Bayer | |
| 2008/0045901 A1 | 2/2008 | Nemoto | |
| 2008/0124028 A1 | 5/2008 | Bickham | |
| 2008/0125713 A1 | 5/2008 | Nemoto | |
| 2008/0173308 A1 | 7/2008 | Schermeier | |
| 2008/0217391 A1 | 9/2008 | Roof | |
| 2009/0050809 A1 | 2/2009 | Holec | |
| 2009/0099552 A1 * | 4/2009 | Levy et al. | 604/533 |
| 2009/0106152 A1 | 4/2009 | Dill | |
| 2009/0224915 A1 | 9/2009 | Angell | |
| 2009/0272794 A1 | 11/2009 | Lange | |
| 2009/0275825 A1 | 11/2009 | Thomas | |
| 2009/0312662 A1 * | 12/2009 | Colman et al. | 600/543 |
| 2010/0047123 A1 | 2/2010 | Solomon | |
| 2010/0111474 A1 | 5/2010 | Satake | |
| 2010/0174495 A1 | 7/2010 | Pereira | |
| 2010/0280948 A1 | 11/2010 | Cohen | |
| 2011/0130720 A1 | 6/2011 | Strobl | |
| 2011/0205074 A1 | 8/2011 | Feng | |
| 2011/0264069 A1 | 10/2011 | Bochenko | |
| 2011/0315757 A1 * | 12/2011 | Colman et al. | 235/375 |
| 2012/0007717 A1 | 1/2012 | Jong | |
| 2012/0037266 A1 * | 2/2012 | Bochenko | 141/1 |
| 2012/0091197 A1 | 4/2012 | Castrec | |
| 2012/0123392 A1 * | 5/2012 | McKinnon et al. | 604/533 |
| 2012/0192987 A1 | 8/2012 | Haschke | |
| 2012/0217307 A1 | 8/2012 | Martin | |
| 2012/0243860 A1 | 9/2012 | Yang | |
| 2012/0290418 A1 | 11/2012 | Itwaru | |
| 2012/0330844 A1 | 12/2012 | Kaufman | |
| 2014/0006184 A1 | 1/2014 | Godsey | |
| 2014/0006195 A1 | 1/2014 | Wilson | |
| 2014/0014729 A1 * | 1/2014 | Colman et al. | 235/487 |
| 2014/0021251 A1 * | 1/2014 | Colman et al. | 235/375 |
| 2014/0025571 A1 | 1/2014 | Dooley | |
| 2014/0031800 A1 | 1/2014 | Ben Oren | |
| 2014/0052114 A1 | 2/2014 | Ben-Oren | |
| 2014/0252082 A1 * | 9/2014 | Colman et al. | 235/375 |
| 2015/0137507 A1 * | 5/2015 | Colman et al. | 285/93 |

FOREIGN PATENT DOCUMENTS

| | | |
|---|---|---|
| JP | 61-38539 | 5/1994 |
| JP | 8-170943 | 7/1996 |
| JP | 8-258153 | 10/1996 |
| WO | 01/75439 | 10/2001 |
| WO | 2004/097994 | 11/2004 |
| WO | 2006/070366 | 7/2006 |
| WO | 2006/119585 | 11/2006 |

* cited by examiner

TUBE VERIFIER

CROSS-REFERENCE TO RELATED APPLICATIONS

The present application is a continuation of U.S. patent application Ser. No. 14/255,724 (published as US 2014/0252082), filed Apr. 17, 2014, which is a continuation of U.S. patent application Ser. No. 13/946,994 (now U.S. Pat. No. 8,720,772), filed Jul. 19, 2013, which is a continuation of U.S. patent application Ser. No. 12/811,361 (now U.S. Pat. No. 8,763,892), filed Jun. 30, 2010, which is the U.S. National Stage of International Application No. PCT/IL2007/001632, filed Dec. 31, 2007, the contents of each of which are expressly incorporated herein in its entirety by this reference.

BACKGROUND

Various analyzing devices, such as, for example, medical devices, use various types of connectors that are used as mediators for connecting between the medical device interface (the instruments itself) and external constituents, such as tubes, cannules, and the like that may be of the disposable type. An example of such medical device is a capnograph, which is an instrument for analyzing exhaled breath. A capnograph samples air that is exhaled by a subject by using a small tube, also known as sample line. One end of the sample line may be connected to an air passageway of a respirator or to a cannula attached to, for example, the subject nostril. The other end of the sampling line is connected, through a connector to the instrument itself. The sampling line, including the tube, the connector and other constituents, such as filters, and the like is, in most cases disposable and is replaced for each patient and for each patient type. For example, a subject which is a child will have a sampling line which is different (for example, in size) than a sampling line of an adult subject.

In general, the shape of a connector is standardized throughout the industry, such that tube assemblies of various manufacturers may be interchangeably used with any analyzing instrument. Hence, the manufacturer of a particular type of analyzing instrument has generally no control over which type of tube is used with his instrument. Therefore, to ensure optimal functioning of the instrument, and for commercial reasons, the manufacturer of an analyzing instrument may want to exert such control. In particular, he may want to stipulate that only a certain class, type and/or model of tube assemblies be connected to, and used with, his instrument. Such a class may, for example, consist of tube assemblies that include a specific constituent, such as, for example, a filter, or such that are manufactured directly by him or to his specifications or under his supervision or license.

Enforcing such stipulation may be performed by various means, such as, for example, by using a unique interlocking key arrangement between the connector and the instrument; having a system by which the correct tube assembly would be identified as such by the instrument, whereupon its operation would be enabled, and to disable the instrument otherwise, such as for example, by using electro-mechanical fitting, electrical fitting, and the like. Benefits of such arrangement would be that the instrument would be prevented from operation also when no tube is connected at all or when even a correct tube is improperly connected, thus avoiding damage to sensitive parts of the instrument and also causing incorrect readings. Yet another purpose may be served by such a system, namely identifying the tube assembly as belonging to one of a number of classes and informing the instrument of the particular identity detected, so as to enable it to automatically operate differently for the different classes.

There is thus a widely recognized need for, and it would be highly advantageous to have, a fluid analysis system that includes the capability of determining that a tube assembly has been properly connected to the analyzing instrument and that the tube is of a certain class. Such a capability should be compatible with the standard shape of connectors being used, as well as with the medical environment, and should be reliable and inexpensive.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other advantages or improvements.

Medical analyzing devices may use various types of connectors that may be used for connecting between the medical device and external constituents, such as tubes, cannules, and the like that are usually disposable and are replaced for each patient. In general, the shape of a connector is standardized, such that tube assemblies of various manufacturers may be interchangeably used with any analyzing device. However, to ensure optimal functioning of the device and for commercial reasons, the manufacturer of an analyzing device may want to stipulate that only a certain class, type and/or model of tube assemblies be connected to and used with his instrument. Such stipulation may be achieved by having an identification and verification means between the medical device and the tube attached to the device. Such capability of determining that a tube assembly has been properly connected to the analyzing instrument and that the tube is of a certain class may further ensure optimal functioning of the medical device. Moreover, the identification and verification means may include any type of information that may be encoded on the end face of the tube connector and identified by the medical device. Accordingly, there is thus provided, according to some embodiments, one or more identification and verification means that may allow increased amount of information to be encoded on the end face of the connector and transferred between the connector and the device. The information encoded may improve the safety of using the device, simplify the use of the device and optimize the use of the device by ensuring an optimal operating mode of the device in accordance with the tube connector (and hence the tube/sampling line) attached to the device. For example, the information encoded on the end face of the connector may be used to determine the type/class and/or model of the connector, such as for example the patient interface, patient size, patient specific parameters, and the like. For example, the information may be used to determine if the connector type is a children's connector (a connector of sampling line that is to be used with children), an adult connector (a connector of sampling lines that is to be used with adults), and the like. This information may be used by the medical device to determine the optimized mode of operation for that type/class/model/manufacturer of connectors and patient interface. This may be achieved, for example, by use of optimized software algorithm to be used for that type of connector and sampling line.

According to some embodiments, there is provided a tube connector for connecting between a fluid sampling tube and a fluid analyzer, the tube connector includes an end face adapted to identify the tube connector, said end face comprising a reflecting surface having one or more reflective regions adapted to reflect light at a predetermined range of wavelengths.

According to some embodiments, the surface of the tube connector may be adapted to reflect light at one or more distinct wavelengths. The surface may further be adapted to selectively reflect light having different intensities. The surface may further include one or more reflective regions having distinct reflective properties. The surface may be patterned, wherein the pattern may include geometrical shapes, non-geometrical shapes, horizontal lines, vertical lines or any combination thereof.

According to some embodiments, the fluid analyzer to which the tube connector is connected to may include a capnograph.

According to further embodiments, the fluid analyzer may include a verification system adapted to identify the connector, wherein the verification system may include one or more light sources and one or more optical detectors. The one or more light sources may include a light emitting diode (LED), a lamp or any combination thereof. The one or more optical detector may include an RGB detector.

According to other embodiments, the end face of the tube connector may further include a Radio Frequency Identifier (RFID) tag adapted to provide further identification of the connector type. The end face of the tube connector may further include a barcode tag adapted to provide further identification of the connector type.

According to additional embodiments, the verification system of the fluid analyzer may further include a Radio Frequency Identifier (RFID) reader, a barcode scanner or both.

According to some embodiments there is provided a device for analyzing fluid, the device includes: a device connector adapted to receive a tube connector and a verification system for identifying the tube connector, wherein said system comprises one or more light sources adapted to transmit light towards an end face of the tube connector, one or more optical detectors adapted to detect reflected light from the end face and to produce a signal indicative of the reflected light and a processor adapted to identify the tube connector type based on a signal received from the detector.

According to some embodiments, the tube connector is adapted to connect between a fluid sampling tube and the fluid analyzer.

According to additional embodiments, the end face of the connector includes a reflecting surface having one or more reflective regions adapted to reflect light at a predetermined range of wavelengths. The end face surface may be adapted to reflect light at one or more distinct wavelengths. The surface may be adapted to selectively reflect light having different intensities. The surface may include one or more reflective regions having distinct reflective properties. The surface may further be patterned, wherein the pattern may include geometrical shapes, non-geometrical shapes, horizontal lines, vertical lines or any combination thereof.

According to additional embodiments, the fluid analyzing device may include a capnograph. The one or more light sources of the verification system may include a light emitting diode (LED), a lamp or any combination thereof. The one or more optical detector of the verification system may include an RGB detector.

According to other embodiments, the end face of the tube connector may further include a Radio Frequency Identifier (RFID) tag adapted to provide further identification of the connector type. The end face of the tube connector may further include a barcode tag adapted to provide further identification of the connector type.

According to additional embodiments, the verification system of the fluid analyzer may further include a Radio Frequency Identifier (RFID) reader, a barcode scanner or both.

According to some embodiments, there is provided a verification system for identifying a tube connector attached to a fluid analyzer, the system includes one or more light sources adapted to transmit light towards an end face of the tube connector; one or more optical detectors adapted to detect reflected light from the end face and to produce a signal indicative of the reflected light; and a processor adapted to identify the tube connector type based on a signal received from the detector.

According to additional embodiments, the verification system may be functionally associated with a device connector adapted to receive the tube connector.

According to additional embodiments, there is further provided a method for identifying a tube connector type attached to a fluid analyzer, the method includes transmitting light from one or more light sources towards an end face of the tube connector; detecting reflected light from the end face by one or more optical detectors, producing a signal indicative of the reflected light and identifying the tube connector based on the signal.

In addition to the exemplary aspects and embodiments described above, further aspects and embodiments will become apparent by reference to the figures and by study of the following detailed descriptions.

BRIEF DESCRIPTION OF THE FIGURES

Examples illustrative of embodiments of the disclosure are described below with reference to figures attached hereto. In the figures, identical structures, elements or parts that appear in more than one figure are generally labeled with a same numeral in all the figures in which they appear. Dimensions of components and features shown in the figures are generally chosen for convenience and clarity of presentation and are not necessarily shown to scale. The figures are listed below.

FIG. 2B—A front view of exemplary end face patterns of a connector, according to some embodiments;

FIG. 2C—A front view of exemplary end face patterns of a connector, according to some embodiments;

FIG. 2D—A front view of exemplary end face patterns of a connector, according to some embodiments;

FIG. 2E—A front view of exemplary end face patterns of a connector, according to some embodiments;

FIG. 2F—A front view of exemplary end face patterns of a connector, according to some embodiments;

FIG. 2G—A front view of exemplary end face patterns of a connector, according to some embodiments;

FIG. 2H—A front view of exemplary end face patterns of a connector, according to some embodiments;

FIG. 2I—A front view of exemplary end face patterns of a connector, according to some embodiments;

FIG. 2J—A front view of exemplary end face patterns of a connector, according to some embodiments;

FIG. 2K—A front view of exemplary end face patterns of a connector, according to some embodiments;

DETAILED DESCRIPTION

In the following description, various aspects of the disclosure will be described. For the purpose of explanation, specific configurations and details are set forth in order to provide a thorough understanding of the disclosure. However, it will also be apparent to one skilled in the art that the embodiments may be practiced without specific details being presented herein. Furthermore, well-known features may be omitted or simplified in order not to obscure the invention.

According to some embodiments, there is provided an end face of a connector, the surface of which may have an annular, ring like shape. The surface of the end face of the connector may be an integral part of the connector, or may be permanently attached to the connector. The surface may include a flat, uniform surface. The surface may include a concave and/or convex surface. The surface may include a patterned surface, wherein the patterns may include recurring patterns of any desired shape. The surface may be a discontinuous surface. The surface may be divided to various regions/areas, wherein at last two areas have different characteristics. By characteristics may include different texture, different compositions, different chemical properties, different optical properties, different electrical properties, different magnetic properties, different surface concaveness, and the like.

Figure 1:
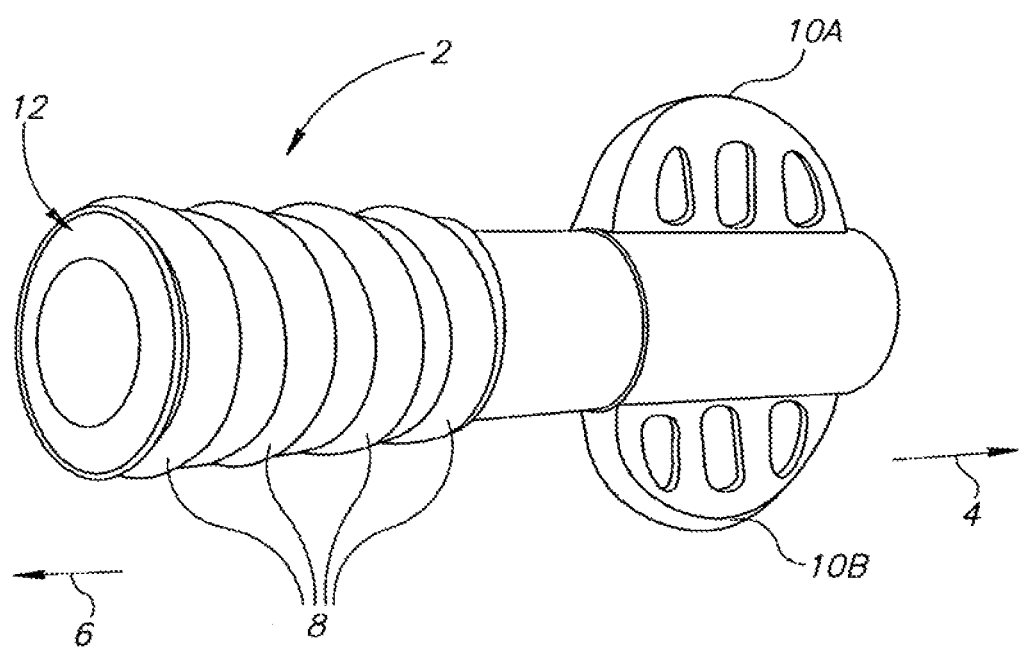
FIG. 1—A perspective view of a connector, according to some embodiments.
Figure 2A:
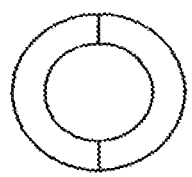
FIG. 2A—A front view of exemplary end face patterns of a connector, according to some embodiments.
Figure 2B:
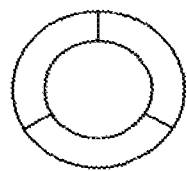
Figure 2C:
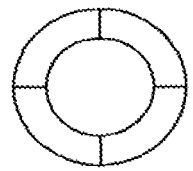
Figure 2D:
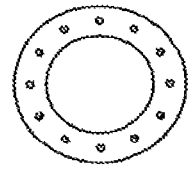
Figure 2E:
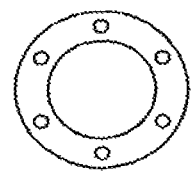
Figure 2F:
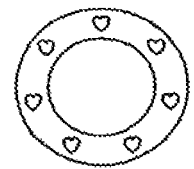
Figure 2G:
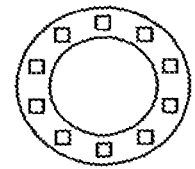
Figure 2H:
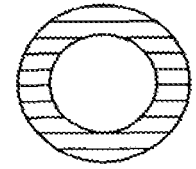
Figure 2I:
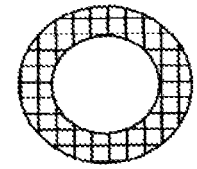
Figure 2J:
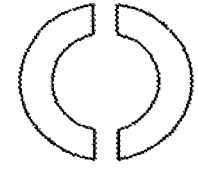
Figure 2K:
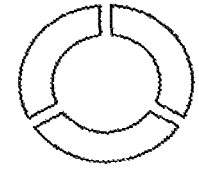

According to some embodiments, there is provided a connector, such as a tube connector that may be used to connect a tube to a medical device, such as for example a capnograph. Reference is now made to FIG. 1, which illustrates a perspective view of a connector, according to some embodiments. The connecter, such as connector (2), may include 2 ends: a tube end (4), which is the end that may be connected to a tube; and a device end (6), which is the end that may be used to connect the connector to a device/instrument. Connector, such as, connector (2) may be a male or a female type connector that may be received/connected/attached/ to a matching female or male connector (referred to herein as a "device connector"), respectively, located on the device, such as, for example, on the device panel. The connector, such as connector (2), may have an elongated cylindrical-like shape. Spiral threads, such as threads (8), may be found at the outer surface of the connector in close proximity to the device end (6) of the connector (2) and may be used to secure the connector to its matching connector on the device (the device connector). At the tube end (4) of the connector (2), gripping wings, (such as, gripping wings 10A-B in FIG. 1) are located. The end face (12) of the device end (6) of the connector (2) may have a circular, annular shape. The end face may form as an integral part of the connector (2), or may be an external surface that is permanently attached to the device end (6) of the connector (2). The end face (12) surface may be a continuous or discontinuous surface, which may include at least two regions/areas that are distinct from each other. By distinct from each other may relate to physical, mechanical, electrical, optical, and chemical properties, such as, for example, but not limited to: shape, pattern, texture, color, size, electrical properties, reflectivity, composition, magnetic properties, and the like, and any combination thereof. The distinct regions of the end face of the connector may be used as an identifying means to the medical device to which the connector is to be connected and consequently to affect a decision process in the device and hence the operation mode of the medical device. The distinct regions of the end face of the connectors may be used to encode data that may be read/identified and used by the medical device. The encoded data may include, for example, the type/class of the connector, the model of the connector, manufacturer of the connector, preferred mode of operation with that connector, and the like.

Prior art, such as that described in U.S. Pat. No. 6,437,316 teaches that the annular end face of the device end may be specularly reflective to light. The reflectivity may be obtained, for example, by coating the surface with a suitable reflective layer, by polishing the surface to a glossy, by hot-pressing a reflective foil and the like. In particular, the reflective surface need not extend over the entire width of the end face, but it must form a complete annular ring. However, such a connector may be identified by the device by only one verification way (meaning—reflection of light at one range of wavelengths). There is thus a need to combine additional verification ways in order to allow the connector to be used with various types/models of devices and also to allow increased amount of information to be encoded on the end face of the connector and transferred between the connector and the device. This may allow a more accurate, efficient, simple and safer mode of operation of medical device.

As referred to herein, the term "the end face of the connector" relates to the end face of the device end of a connecter, such as connector 2 of FIG. 1, unless otherwise stated.

As referred to herein, the terms "amplitude" and "intensity" may interchangeably be used.

As referred to herein the term "type", "model", "class" of the connector may interchangeably be used and may relate to the interface to be used with the tube connector and/or manufacturer of the tube connector.

According to some embodiments, the end face of the connector may include more than one region with distinct reflectivity characteristics. The regions may be adjacent to each other or may be spatially separated. Each of the regions may be reflective at a different range of wavelength and/or possess different level (amplitude, intensity) of reflectivity and/or may be non-reflective (such as, for example, colored black, which absorb all light and does not reflect back). For example, the end face may include two spectrally distinct reflective regions. Each of the regions may comprise about half of the annular circumference of the end face. For example, one region may be spectrally reflective such that when light is emitted at the end face, this region may reflect at one amplitude, while the second region may reflect at a second amplitude. For example, one region may be spectrally reflective such that when light is emitted at the end face, this region may reflect light at one wavelength (for example, at the green color range of wavelength), while the second region may reflect light at a second wavelength (for example, at the red color range of wavelengths). The reflected lights may be detected by matching detectors located in the medical device and then further processed/analyzed to confirm the connection between the connector and the medical device, as further detailed below herein. The distinct regions of reflectivity of the connector end face may be coated or comprised of various materials that possess different reflectivity characteristics. For example, the distinct regions may have reflective materials that contain dyes or pigments. For example, the distinct regions may be coated with suitable spectral filters. For example, the distinct regions may have different surface areas, such as, for example, a flat surface, a concaved surface, a convex surface or any combination thereof.

According to some embodiments, in addition to determining various wavelength ranges of reflectivity of connectors with more than one reflective region at their end face, the amplitude and the threshold levels of reflectivness may also be determined. The threshold levels of reflectiveness may be used as an additional data encoding means that may be used to distinguish between various types/models of connectors. For example, a connector that exhibits reflectivity of above a predetermined threshold value may belong to a certain type of connector (for example, connectors of sampling lines that are to be used with children), while connectors with a lower threshold (that may include, for example, at least two distinct regions of reflectivity at the connector end face) may belong to a different type of connector (for example, connectors of sampling line to be used with adults). For example, the threshold levels may be used to distinguish between connectors manufactured by different manufacturers.

According to further embodiments, the end face of the connector may include various patterns that may be distinguished by their characteristics/properties. The patterns may include any shape, such as geometrical shapes (such as circles, triangles, squares, and the like), non-geometrical shapes, such as hearts, droplets, waves, and the like. The patterns may further include any combination of shapes. The shapes may include any size and any number of shapes that may be distributed evenly or non-evenly over the surface of the end face of the connector. The patterns may include recurrent patterns. The patterned regions on the surface of the end face connector may exhibit different characteristics than the non-patterned region surface. Different characteristics may include, for example, optical characteristics, such as, for example, various reflectivness properties.

According to additional embodiments, the end face of the connector may include any combination of lines, dots, spots and the like that may be distributed evenly or non evenly over the surface of the end face of the connector. For example, the lines may include straight lines, curved lines, checkered lines, and the like. Areas/regions defined by the combination of lines may possess different characteristics than other regions. Different characteristics may include, for example, optical characteristics, such as, for example, various reflectivness levels, various wavelength ranges of the reflected light, and the like. According to further embodiments, the surface of the end face of the connector may include one or more concave regions and one or more convex regions. The concave regions may focus the reflected light and the convex regions may defocus the reflected light and thus different levels of reflectivity from different regions of the end face of the connector may be obtained.

Reference is now made to FIGS. 2A-K, which illustrate exemplary end faces of a connector according to some embodiments. For example, end face A illustrates an annular end face of a connector with two regions with distinct reflective properties. For example, end face B illustrates an annular end face divided into three equal regions, wherein at least one of the regions has distinct reflective properties. For example, end face C illustrates an annular end face divided into four equal regions, wherein at least one of the regions has distinct reflective properties. For example, end face D illustrates an annular end face of a connector with a reflective surface and spots, at least one of which is with distinct reflective characteristics. For example, end face E illustrates an annular end face of a connector with a reflective surface and circles distributed over the surfaces, at least one of the circles exhibits distinct reflective characteristics. For example, end face F illustrates an annular end face of a connector with a reflective surface and heart shaped regions distributed over the surfaces, at least one of the heart shaped regions exhibits distinct reflective characteristics. For example, end face G illustrates an annular end face of a connector with a reflective surface and squares distributed over the surfaces, at least one of the squares exhibits distinct reflective characteristics. For example, end face H illustrates an annular end face of a connector with a reflective surface and horizontal lines stretched over the surface, at least one of the areas bound between the lines exhibits distinct reflective characteristics. For example, end face I illustrates an annular end face of a connector with a reflective surface and horizontal and vertical lines distributed over the surface, at least one of the areas bound between the lines exhibits distinct reflective characteristics. For example, end face J illustrates an annular end face of a connector divided into two separate, non-continuous regions, wherein at least one of the regions has distinct reflective properties. For example, end face K illustrates an annular end face of a connector divided into three separate, non-continuous regions, wherein at least one of the regions has distinct reflective properties. For example, end face L illustrates an annular end face of a connector divided into four separate, non-continuous regions, wherein at least one of the regions has distinct reflective properties.

According to some embodiments, the medical device may include a verification system that may be used to detect/identify the connector (and hence the tube) attached to the medical device. Identification/detection of the connector that is attached to the medical device may be performed by detection/identification of any of the properties/parameters of the end face of the connector that are described herein. For example, the verification system of the medical device may detect/identify the optical properties (as determined by the reflectiveness properties) of the end face of the connector. The verification system may include one or more optical light source emitters (such as, for example, Light Emitting Diodes (LEDs)) that may emit light at various individual wavelengths and/or at a wide spectral range of wavelengths. For example, the light source may include a Light Emitting Diode (LED) that may emit light at the visible white light spectral range (for example, at the range of 0.4 to 0.7 mm) The verification system may further include one or more optical receivers that may be adapted to receive light reflected from the end face surface of the connector. The optical receivers may be spatially separated from the light source emitters so as to ensure that light detected by the optical receivers is the light reflected from the end face surface of the connector. Spatial separation may be performed, for example by placing an optical barrier between the light source and the optical receiver. The spatial separation may be performed, for example, by use of optical wave guides that may be used to create a channel/chamber, at the bottom of which the optical detector is situated. The use of such a chamber may ensure that only light that is reflected from the end face surface of the connector reaches the optical receiver, while light, such as scattered light from the environment, direct light from the light source, and the like, is prevented from reaching the optical detector. The reflected light from the end face of the connector may be at various wavelengths and at various amplitudes (intensity levels), which may be determined by the reflective properties of the surface of the end face connector. The optical receiver may include any type of light and/or color detector. The optical receiver may include more than one optical receiver, which may be adapted to receive light at the wavelengths, which correspond to the wavelengths of the light reflected from the various regions of the end face of the connector. For example, the optical receiver may include one or more light detectors that may be used to detect intensity of reflected light. The optical receiver may include a light detector that may be further equipped with an optical filter that may allow the optical detector to identify a specific, predetermined range of wavelengths that correspond to the optical filter. For example, the optical detector may include an RGB detector, which is well known in the art. Briefly, an RGB detector may be basically described as a multi-element photodiode coupled to red, green, and blue filters, that enable the photodiode to generate separate response curves for the three colors and hence determine the color (wavelength) and the amplitude (intensity) of the light detected by the photodiode. As such, the RGB color detector that may be used to detect light of various wavelengths (which correspond to different colors) may be reflected from one or more surfaces of the end face of the connector. The RGB detector may further be used to detect the amplitude (level) of the reflected light from one or more surfaces of the end face of the connector. According to additional embodiments, the optical receiver may be adapted to receive light at a wavelength which corresponds to the wavelength of the light reflected from a region of the end face of the connector and to further receive light at a second wavelength, which may correspond to the wavelength of the light reflected from other region(s) of different reflectivity of the end face surface. According to other embodiments, the light reflected from the regions of different reflectivity on the surface of the end face of the connector may be conveyed by the use of, for example, optical fibers that may collect the signals reflected from the individual spots into one optical signal that may be received by the second receiver.

Figure 3A:
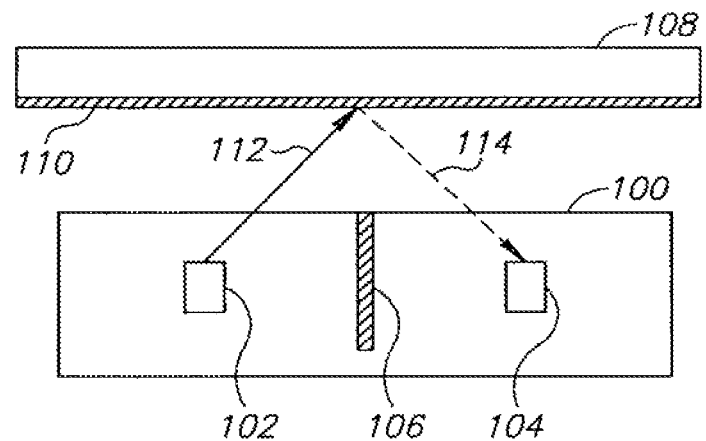
FIG. 3A—A perspective schematic of a closeup side view of a connector and verification system, according to some embodiments, and FIG. 3B—A perspective schematic of a closeup side view of a connector and verification system, according to some embodiments.
Figure 3B:
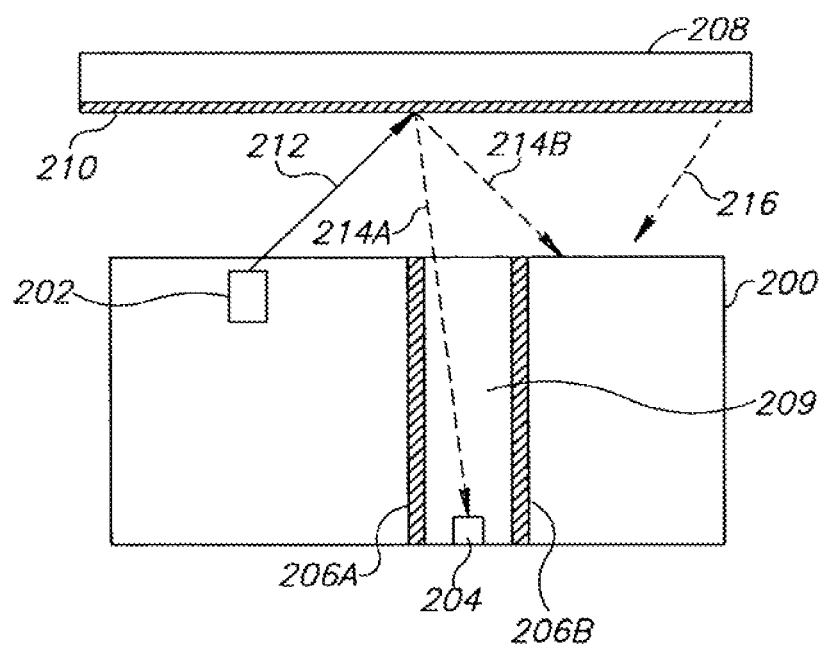

Reference is now made to FIG. 3, which illustrates a schematic drawing of a close up side view of an end face of a tube connector and the medical device verification system, according to some embodiments. As shown in FIG. 3A, verification system 100, includes one or more light sources (shown as one light source, 102). The light source may include, for example, a LED that may emit light a the white light spectral range. The verification system further includes one or more optical receivers (shown in FIG. 3A as one optical receiver, 104). The optical receiver may include, for example an RGB detector. The verification system may further include an optical barrier, such as optical barrier 106, that may be used to prevent light emitted from a light source (such as light source 102) from directly reaching the optical receiver (such as optical receiver 104). Also shown in FIG. 3A, the end of connector, (such as connector 108) and the end face surface of the connector, (end face 110). When operating, the verification system light source may emit light (illustrated as arrow 112). The light emitted from the light source may be reflected (illustrated as reflected light (arrow 114)), depending on the reflectiveness properties of the connector end face (110). Reflected light 114 may reach the optical receiver 104, that may consequently determine the optical properties of the reflected light (such as color (wavelength) and amplitude (intensity). According to the determined optical properties of the reflected light, the verification system (as detailed below herein) may determine the type/model of the connector attached and further determine the operation mode of the medical device. As shown in FIG. 3B, verification system 200, may include one or more light sources (shown as one light source, 202). The light source may include, for example, a LED that may emit light at the white light spectral range. The verification system further includes one or more optical receivers (shown in FIG. 3B as one optical receiver, 204). The optical receiver may include, for example an RGB detector. The verification system may further include one or more optical guides, such as optical guides 206A-B that may form a tunnel/chamber, such as chamber 209, at the bottom of which, optical receiver (204) is positioned. The optical guides may be used to prevent light emitted from a light source (such as light source 202) from directly reaching the optical receiver (such as optical receiver 204), as well as other light that is not reflected from the connector end face. Also shown in FIG. 3B is the end of connector, (such as connector 208) and the end face surface of the connector, end face 210). When operating, the verification system light source may emit light (illustrated as arrow 212). The light emitted from the light source may be reflected (illustrated as reflected lights (arrow 214A-B)), depending on the reflectiveness properties of the connector end face (210). Only light that is reflected at an acute angle (such as reflected light 214A) may enter chamber 209 and reach the optical receiver. Other reflected light (such as 214B) is prevented from reaching the optical receiver. Likewise, light that may originate from other sources, such as scattered light from the environment (demonstrated as arrow 216) is prevented from reaching the optical receiver. The optical receiver that may consequently determine the optical properties of the detected reflected light (such as color (wavelength) and amplitude (intensity)). According to the determined optical properties of the reflected light, the verification system (as detailed below herein) may determine the type/model of the connector attached and further determine the operation mode of the medical device. Additional elements/constituents of the verification system that are detailed below herein, such as wires, fibers, power sources, electrical circuits, comparators, integrators, and the like are omitted from drawings 3A and 3B for clarification purposes.

According to some embodiments, and as mentioned above herein, the medical device may include a verification system that may be used to de-encode the data encoded on and by the end face of the connector. The verification system may be used to analyze the properties and characteristics of the connector attached to the medical device, and accordingly change the mode of operation of the device. For example, in relation to detection of reflected light by the end face of the connector, the medical device may include the various electrical circuits that may further include various constituents for generating and processing optical signals transmitted to the connector end face and received therefrom and based upon the analyzed results determine if the connector is properly connected to the medical device and identify what is the type, class, model and/or interface of the connector (and hence the tube attached thereto). According to some embodiments, the electronic circuits may include several constituents, such as, for example, but not limited to: one or more light sources (such as, for example, LED adapted to emit light at various wavelengths, Infra Red light source, Ultraviolet light source, laser light source, and the like); photodiodes adapted to receive emitted and reflected light and convert the signal to electrical signal; RGB detector; fibers, such as optical fibers adapted to transfer light (emitted and reflected) between the medical device and the connector; one or more amplifiers adapted to specifically amplify the light reflected from the connector end face; filters, adapted to emit and/or receive reflected light of a specific wavelength; one or more synchronous detectors adapted to synchronize light pulses emitted from the one or more light sources, respectively; one or more integrators adapted to receive a voltage signal from the one or more synchronous detectors and integrate the voltages over a certain time period to yield voltage values (for each of the light sources); one or more comparators/processors which are adapted to compare/process the voltage value obtained by the one or more integrators to predetermined threshold values that correspond to the various light reflections from the connector. The one or more processors may be adapted to process the information received from the detectors and to provide identification of the tube connector based on the signals received from the detector. The one or more comparators/processors may yield a signal that may be used by the medical device to determine if the connector is properly attached to the device and if the connector is of the right type, class and/or model and accordingly modify the operation of the medical device. If, for example, the binary signal received indicates that improper connection is detected between the device and the connector, the device may not operate until the attachment is corrected. For example, if the signal indicates that the connector is attached to a sampling line (tube) adapted for children, than the device may operate accordingly and be adjusted (for example, automatically) to operate under "children" mode. For example, if the calculated/measured signal is indicative that the connector is attached to a sampling line that is to be used with intubated patients, the device may operate accordingly and be adjusted to operate under "intubated patient" mode. In addition, the verification system of the medical device may further include one or more additional detectors/receivers that may be used to detect/sense/measure/receive additional features/characteristics/properties/information that may be encoded on and by the end face of the connector, as further detailed below herein.

According to some embodiments, the identification of the connector (and hence the tube) being attached to the medical device may be performed in various ways, such as, for example, while the connectors are being attached ("on the fly"), after the connectors have been attached ("final position") or any combination thereof. For example, the identification (and verification) of the tube connector being attached may be performed on the fly, during the attachment (connection) of the tube connector to its corresponding connector on the device. The connection may be performed, for example by pushing and/or turning and/or screwing the tube connector to its location in the device connector. During the time of insertion, the tube connector may be identified by the verification system by any of the methods described herein, such as, for example, by identifying distinct regions of reflectivity (amplitude and/or wavelength) of the end face of the connector; by identifying recurring changes of reflectivity during the revolving of the tube connector relative to the device connector, and the like. The identification (and verification) of the tube connector attached to the device may be performed after the tube connector is attached to its respective device connector, while the connectors are at their final (resting) position. Such identification may be performed by the verification system of the medical device by any of the methods described herein.

According to some embodiments, the relative final location (alignment) of the end face of the connector with respect to the detectors/receivers of the verification system of the medical device may be determined. For example, the relative location (alignment) of the end face of the connector with respect to its matching device connector may be determined Determining a desired relative location of the end face of the connector to its matching device connector may be used to allow proper alignment between the respective locations of the two connectors and hence, a desired respective location between the end face of the connector to the verification system of the medical device. Proper alignment may be used to allow matching between regions of the end face of the connector and, for example, respective receivers/detectors (such as, for example, optical receivers) of the verification system of the medical device. Determination of the desired relative location (alignment) between the end face connector and the verification system of the medical device may be performed by various means, such as, for example but not limited to physical barriers, mechanical fitting, visual fitting, manual fitting, and the like. For example, proper alignment may be achieved by matching projection(s) and depression(s) on the end face connectors and its matching device connector; key and lock fittings on the end face connector and its matching device connector; markings on the end face connector and its matching device connector, to which it is to be attached, and the like. For example, the end face connector may include projection at the circumference of the device end of the connector. The device connector may include a matching depression. In order to physically attach the two connectors, the respective projection and depression must match. Matching the respective projections and depression of the connectors ensures the proper relative alignment of the end face of the connector with the corresponding receivers/detectors of the verification system of the medical device. In such a manner, different regions of the end face of the end face connector may be distinguishable and may allow identification and/or verification of the end face and further, the tube being used. For example, the end face connector may include a marking, such as a line, at the circumference of the device end of the connector. Likewise, the connector device may include a marking, such as a line, at the circumference of the device connector. After (or during) attaching the connectors, the two markings on the two connectors must be aligned. Alignment of the markings on the connectors ensures proper relative alignment of the end face of the connector with the corresponding receivers/detectors of the verification system of the medical device. In such a manner, different regions of the end face of the connector may be distinguishable and may allow identification and/or verification of the end face and hence the tube being used.

According to some embodiments, the threshold values may be chosen to be such that would discriminate between integrated voltage values that result from the reflection of light from various regions of the end face of the connector and other sources of light. The threshold values may further be used to discriminate between various types of connectors, such as, for example, between connectors that may have only one reflective region on the end face and connectors that may have more than one reflective region on their end face. In addition, the threshold values may be used to discriminate between connectors that have one or more reflective regions on their end face and connectors that have no reflective regions on their end face. In addition, the threshold values may be used to discriminate between various types, classes and/or models of connectors, that may be adapted for various uses (for example, use with children sampling lines, adults sampling lines, and the like).

According to some embodiments, the end face of the connector may include an additional distinguishing feature in addition to being reflective. For example, the additional feature may include radioactive labeling of at least a distinct region of the end face. The radioactive labeling may include spots deposited along the annular circumference of the end face of the connector. The radioactive spots may include radioactive labeling using any common radioisotope, such as, for example, deuterium ($H^3$), $C^{14}$, $P^{32}$, $S^{35}$ and the like. In addition, the medical device verification system may include an appropriate matching radioactive detector, such as a radioactive counter that may be used to detect radioactive energy emitted from the connector end face.

According to some embodiments, the end face of the connector may include an additional distinguishing feature in addition to being reflective. For example, the end face of the connector may include an electronic identification means, such as, for example, a Radio Frequency Identification (RFID). RFID is known as an automatic identification method, that stores and remotely retrieves data using RFID tags or transponders. An RFID tag is an identification tag that may be identified wirelessly using radio waves. Most RFID tags include at least two parts: an integrated circuit for storing and processing information, modulating and demodulating a radio frequency signal; and an antenna for receiving and transmitting the signal. In addition, a technology called chipless RFID allows for discrete identification of tags without an integrated circuit. According to some embodiments, an RFID tag may be implemented with the connector. The RFID tag may preferably be implemented at the end face of the connector, for example, by using a chipless RFID that may be printed on at least a region of the end face of the connecter. The RFID tag may be of the passive type, which is a tag that does not need an autonomous power supply. The RFID tag may include specific information characteristic of the connector, such as type, class and model of the connector. In addition, the verification system of the medical device may include an antenna and an RFID reader that may identify the RFID tag and read/process the information encoded within the RFID tag. For example, the RFID tag may include information regarding the type, class and model of the connector (for example, for what type of patient it is to be used with: a child or an adult; intubated patient or non-intubated patient; who is the manufacturer that produced the connector, and the like).

According to some embodiments, the end face of the connector may include an additional distinguishing feature in addition to being reflective. For example, the end face of the connector may include a barcode pattern that may be present on at least one region of the end face of the connector. The barcode may be used to identify the connector type/model to the medical device to which it is to be connected. In addition, the medical device verification system may further include an appropriate barcode reader, such as, for example, a barcode scanner, that may be used to detect the presence of a barcode on the end face and to further interpret the barcode. The bar code may be read "on the fly", while the connector is being turned/screwed into its location towards its final position. Identification of the barcode by the medical device verification system may allow proper identification of the connector that is connected to the medical device and accordingly, adjust the operation mode of the medical device.

According to some embodiments, the end face of the connector may include an additional distinguishing feature in addition to being reflective. For example, the end face of the connector may include one or more regions that include distinct magnetic field characteristics. The one or more regions with the distinct magnetic properties may be of any shape and size. The distinct magnetic properties may be achieved by, for example, using a coating, which has magnetic properties, that may be applied to the appropriate region on the end face. In addition, the medical device verification system may further include an appropriate magnetic field detector, that may be used to detect the presence and/or force of the magnetic field created by the one or more regions of the end face.

According to some embodiments, the end face of the connector may include an additional distinguishing feature in addition to being reflective. For example, the end face of the connector may include one or more regions that include distinct electrical field characteristics. The one or more regions with the distinct electrical properties may be of any shape and size. The distinct electrical properties may include, for example, regions with different electrical conductance, different electrical field, different electrical energy produced thereby, and the like. The distinct electrical properties may be applied by, for example, applying small electrical power to specified one or more regions on the end face. In addition, the medical device verification system may further include an appropriate electrical detector, that may be used to detect the presence and/or force of the electrical energy and/or current and/or conductance and/or electrical filed created by the one or more regions of the end face with distinct electrical properties.

According to some embodiments, the end face of the connector may include an additional distinguishing feature in addition to being reflective. For example, the use of pressure drop detection across the sampling line used may also be used as a verification method to determine if the connector is of the appropriate class, type, an/or model. Detection of pressure drop may be performed, for example, initiating operation of the medical device upon first verification of correct attachment between the connector and the medical device. Then, different pressure drops across the sampling line are created and detected. The different pressure drops, which are characteristics of a sampling line, may be detected and may thus identify the sampling line used with the attached connecter. If the pressure drop identifies a connector/sampling line that is not of the required/desired type (such as, for example, not by the desired manufacturer), the operation of the medical device may stop until a proper connector and sampling line are attached to the device.

According to further embodiments, the end face of the connector may include one or more light sources. The light sources may include, for example, one or more LED that may emit light at various, distinct wavelengths. The one or more LED may receive power from an internal power supply, such as, for example, small batteries located within the cavity of the connector. The LEDs may emit light at predetermined wavelength ranges that may match corresponding light detectors, such as, for example, photodiodes, located in the verification system of the medical device. The light detectors may convert the detected light to a binary signal, as detailed above herein to determine the type, class and/or model, of the connector and to determine the correct assembly of the connector to the medical device. If the connector is properly attached to the medical device and is of the appropriate type, the device may operate in an operation mode that is suitable for the detected connector.

While a number of exemplary aspects and embodiments have been discussed above, those of skill in the art will recognize certain modifications, permutations, additions and sub-combinations thereof. It is therefore intended that the following appended claims and claims hereafter introduced be interpreted to include all such modifications, permutations, additions and sub-combinations as are within their true spirit and scope.

What we claim is:

1. A tube connector, comprising:
    a circular annular end face configured to be inserted into a tube connection system and illuminated by the tube connection system, at least a portion of the circular annular end face comprising at least a first spectrally distinct reflective region, at least a second spectrally distinct reflective region and at least a third spectrally distinct reflective region, said first and second spectrally distinct reflective regions positioned at different regions of said circular annular end face, said first spectrally distinct reflective region configured to reflect light at a first wavelength when illuminated by the tube connection system, said second spectrally distinct reflective region configured to reflect light at a second wavelength when illuminated by the tube connection system, the first wavelength being different from the second wavelength, said third spectrally distinct reflective region configured to reflect light at a third wavelength when illuminated by the tube connection system, the third wavelength being different from both the first and second wavelengths, and wherein tube connector is configured to provide encoded data controlling operation of the tube connector system, via the three spectrally distinct reflective regions, when the tube connector is inserted into and the encoded data read by the tube connection system.

2. The tube connector of claim 1, wherein said first spectrally distinct reflective region is configured to reflect light at the first wavelength when illuminated by a first light source in the tube connection system and said wherein second spectrally distinct reflective region is configured to reflect light at the second wavelength when illuminated by a second light source in the tube connection system.

3. The tube connector of claim 1, wherein said circular annular end face is configured to encode data indicative of a type of said tube connector.

4. The tube connector of claim 1, wherein said circular annular end face is configured to encode data indicative of a preferred mode of operation of said tube connector.

5. The tube connector of claim 1, wherein said at least two spectrally distinct reflective regions comprise at least one geometrical shape.

6. The tube connector of claim 1, wherein the at least two spectrally distinct reflective regions include at least one concave region and at least one convex region.

7. The tube connector of claim 1, wherein the at least two spectrally distinct reflective regions cover a substantial portion of said tube connector.

8. The tube connector of claim 1, wherein the circular annular end face comprises a pattern of at least three equal regions.

* * * * *